(12) United States Patent
Nordström et al.

(10) Patent No.: US 10,888,711 B2
(45) Date of Patent: Jan. 12, 2021

(54) METHODS FOR INVERSE PLANNING (71) Applicant: ELEKTA INSTRUMENT AB, Stockholm (SE)

(72) Inventors: Håkan Nordström, Sollentuna (SE); Björn Somell, Stockholm (SE); Stella Riad, Sundbyberg (SE); Jens Sjölund, Sundbyberg (SE)

(73) Assignee: ELEKTA INSTRUMENTS AB, Stockholm (SE)

( * ) Notice: Subject to any disclaimer, the term of this patent is extended or adjusted under 35 U.S.C. 154(b) by 116 days.

(21) Appl. No.: 16/282,169

(22) Filed: Feb. 21, 2019

(65) Prior Publication Data

US 2019/0255355 A1    Aug. 22, 2019

Related U.S. Application Data

(60) Provisional application No. 62/633,437, filed on Feb. 21, 2018.

(51) Int. Cl.
*A61N 5/10* (2006.01)
*G06N 20/00* (2019.01)

(52) U.S. Cl.
CPC ......... *A61N 5/1031* (2013.01); *A61N 5/1065* (2013.01); *A61N 5/1071* (2013.01);
(Continued)

(58) Field of Classification Search
CPC .... A61N 5/103; A61N 5/1031; A61N 5/1032; A61N 5/1045; A61N 5/1077; A61N 5/1071; A61N 2007/0086; A61N 5/10
See application file for complete search history.

(56) References Cited

U.S. PATENT DOCUMENTS

2011/0091014 A1    4/2011  Siljamaki et al.
2016/0051840 A1*   2/2016  H Rdemark ......... A61N 5/1031
                                                    600/1
(Continued)

FOREIGN PATENT DOCUMENTS

CN    107708806 A       2/2018
WO    WO 2005/072825 A1 8/2005
WO    WO 2016/198979 A1 12/2018

OTHER PUBLICATIONS

Ehrgott et al: "Operations Research Methods for Optimization in Radiation Oncology"; Jan. 1, 2017, XP055604592; pp. 1-41
(Continued)

*Primary Examiner* — Don K Wong
(74) *Attorney, Agent, or Firm* — Birch, Stewart, Kolasch & Birch, LLP (57) ABSTRACT

In the field of radiotherapy, methods for dose or treatment planning for a radiotherapy system are disclosed, wherein a spatial dose delivered can be adjusted and delivered radiation is determined using an optimization problem that steers the delivered radiation according to a frame description reflecting criteria for regions of interest that include at least one of targets to be treated during treatment of the patient, organs at risk and/or healthy tissue. The method includes estimating a voxel set receiving a higher dose than a predetermined threshold dose level, which voxel set includes voxels from at least one target volume. Further, a low dose voxel set is determined and a frame description for the voxels in the low dose voxel set is provided where voxels receiving a dose exceeding a predetermined threshold value is penalized such that the dose delivered to the low dose voxel set is suppressed. The frame description is then used in the optimization problem that steers the delivered radiation.

25 Claims, 8 Drawing Sheets

Fig. 6

(52) U.S. Cl.
CPC ............ *G06N 20/00* (2019.01); *A61N 5/1001* (2013.01); *A61N 5/1081* (2013.01); *A61N 5/1084* (2013.01); *A61N 2005/1041* (2013.01)

(56) References Cited

U.S. PATENT DOCUMENTS

2017/0177812 A1    6/2017   Sjölund
2019/0255354 A1*   8/2019   Nordstrom ............. G16H 20/40

OTHER PUBLICATIONS

European Search Report from EP 19157753.5, dated Jul. 23, 2020; pp. 1-9.

* cited by examiner

METHODS FOR INVERSE PLANNING

CROSS REFERENCE TO RELATED APPLICATIONS

This non-provisional application claims the benefit under 35 U.S.C. § 119(e) to U.S. Provisional Application No. 62/633,437, filed on Feb. 21, 2018, which is hereby expressly incorporated by reference into the present application.

FIELD OF THE INVENTION

The present invention relates to the field of radiotherapy. In particular, the invention relates to methods and systems for planning and optimizing treatment sessions of a patient in radiotherapy systems.

BACKGROUND OF THE INVENTION

The development of surgical techniques has made great progress over the years. For instance, patients in need of brain surgery may instead have non-invasive surgery which drastically reduces the trauma to the patients.

Systems for non-invasive surgery include the Leksell Gamma Knife® Icon™ and the Leksell Gamma Knife® Perfexion, which provide such surgery by means of gamma radiation. The radiation is emitted from a large number of fixed radioactive sources and is focused by means of collimators, i.e. passages or channels for obtaining a beam of limited cross section, towards a defined target or treatment volume. Each of the sources provides a dose of gamma radiation which, by itself, is insufficient to damage intervening tissue. However, tissue destruction occurs where the radiation beams from a plurality of radiation sources intersect or converge, causing the radiation to reach tissue-destructive levels. The point of convergence is hereinafter referred to as the "focus point".

Treatment plan optimization in radiotherapy, including for example gamma knife radiosurgery, aims at delivering sufficiently high dose to the target volume within the patient (e.g. in treatment of tumours) at the same time as the dose delivered to adjacent normal tissue is minimized. In treatment plan optimization, at least three competing factors have to be considered: delivering a sufficiently high dose to the target volume, sparing the surrounding normal or healthy tissue and keeping the treatment time as short as possible.

The treatment plan optimization is a process including optimizing the relative isocenter locations or beam directions, the beam shape settings (e.g. collimator configuration) and the fluences. In, for example, the Leksell Gamma Knife® Icon™ and the Leksell Gamma Knife® Perfexion the treatment plan optimization may include optimizing the number of shots being used, the collimator configuration of each shot, the shot times, and the position of the shot. The irregularity and size of a target volume greatly influence relative isocenter locations or beam directions, the beam shape settings (e.g. collimator configuration) and the fluences used to optimize the treatment.

In treatment planning, inverse treatment planning has gained more and more interest. Inverse planning generally refers to the stage in treatment planning where a deliverable treatment plan is sought, such that a number of criteria are satisfied. Inverse planning can be contrasted to forward planning, where the operator manually places, weights and shapes shots. The promises of inverse planning are shorter planning times and higher quality plans. Inverse planning is sometimes tightly integrated with forward planning, e.g. in the software accompanying the Leksell Gamma Knife: Leksell GammaPlan®. It is based on relative isodoses and uses metrics that are well-known in radiosurgery. This facilitates the transition from forward to inverse planning, and is presumably one of the reasons for the widespread adoption of inverse planning. A downside of relative isodose-based inverse planner and the complexity of the objectives is that the resulting optimization problem is inherently difficult to solve. In realistic cases it requires a compromise between computation time and the risk of ending up in a poor local optimum. This makes it difficult to explore what trade-offs are achievable—especially in complicated cases with multiple conflicting objectives. For example, a multi-metastases case where at least one metastasis is adjacent to an organ at risk. Incidentally, in such a case it might also be desirable to specify some criteria that must be met. In present inverse planners criteria for organs at risk (OAR) cannot be set.

Historically in inverse treatment planning for Gamma Knife radiosurgery, the relative isodoses are the fundamental object of interest. This is a heuristic motivated by the dose fall-off being the steepest for a certain isodose level, which should coincide with the target boundary. Incidentally, this is true for a single shot but need not be true when the dose distribution is the sum of contributions from multiple shots. Note that utilizing steep gradients presupposes high positional accuracy. For an isocenter the optimization variables are the position, collimator configuration and beam-on time. The isocenter locations are moved during the optimization and the collimator configuration is treated as a discrete element in the set of all possible collimator configurations. Organs at risk are not handled explicitly in the objective function, which can be a severe limitation. Evidently, tolerance doses for organs at risk are given in absolute dose but in the present mode of planning, absolute dose is assigned only after completing the plan. This results in an optimization problem that is very hard in the sense that any solution method requires either extensive computations or runs the risk of returning unsatisfactory solutions.

In improved inverse treatment planning methods provided by the applicant, a number of objectives reflecting clinical criteria for regions of interest, including targets to be treated during treatment of the patient, organs at risk and/or healthy tissue are set and radiation dose profiles to be delivered to the target are generated. A convex optimization problem that steers the delivered radiation according to the objectives is provided and dose profiles for specific treatment configurations including beam shape settings for the radiation dose profiles are calculated using the convex optimization problem. Thereafter, a treatment plan, including determining the radiation dose profiles to be delivered during treatment based on the treatment configurations are created, wherein each radiation dose profile is modelled by a spatial dose volume distribution of radiation, the shape of the spatial distribution depending on the beam shape settings and an optimal treatment plan that satisfies the clinical criteria is selected.

However, there is an abundance of clinical data showing that adverse cognitive effects may occur if large volumes of normal tissue is irradiated by also relatively low dose. Thus, an important objective of planning methods is therefore to achieve as low dose delivery to the normal tissue surrounding the target volume or target volumes, which is especially difficult when multiple targets are close to each other. A main problem in the optimization is that the set of voxels in the irradiated volume depends on the dose distribution and will change during the optimization leading to a non-convex optimization problem, which generally is difficult to solve.

Thus, there is still a need of more efficient methods for planning and optimizing the treatment.

SUMMARY OF THE INVENTION

An object of the present invention is to provide improved methods and systems for planning and optimizing treatment sessions of a patient treated by radiotherapy.

This and other objects are fulfilled by the present invention as defined by the independent claims. Preferred embodiments are defined by the dependent claims.

The term "target" or "target volume" refers to a representation of a target of a patient to be treated during radiotherapy. The target may be a tumour to be treated with radiotherapy. Typically, the representation of the target is obtained by, for example, non-invasive image capturing using X-ray or nuclear magnetic resonance.

The term "shot" refers to a delivery of radiation to a predetermined position within a target volume having a predetermined level of radiation and a spatial distribution. The shot is delivered during a predetermined period of time ("beam-on" time) via at least one sector of the collimator of the therapy system using one of the states of the sector. A "composite shot" refers to the delivery of radiation to a focus point using different collimator sizes for different sectors.

The term "beam-on time" refers to the predetermined period of time during which a shot is delivered to the target volume.

The term "constraint" refers to constraints on the optimization variable, either directly, e.g. enforcing non-negative beam-on times, or indirectly, e.g. enforcing a minimum dose delivery to a certain volume. Also, constraint may refer to constraints that must not be violated (hard constraints) and/or constraints for which violations are allowed but penalized in the objective function (soft constraints).

The term "voxel" is used in the context of this application and refers to volume elements on a grid, which may be anisotropic in a three-dimensional space.

The term "frame description" includes at least an objective function and/or constraint for a set of voxels.

The present invention can, for example, be used in radiotherapy. Radiotherapy is used to treat cancers and other ailments in mammalian (e.g., human and animal) tissue. One such radiotherapy device is a Gamma Knife, which irradiates a patient with a large number of low-intensity gamma rays that converge with high intensity and high precision at a target (e.g., a tumour). Another radiotherapy device uses a linear accelerator, which irradiates a tumour with high-energy particles (e.g., photons, electrons, and the like). Still another radiotherapy device, a cyclotron, uses protons and/or ions. Another form of radiotherapy is brachytherapy, where a radiation source is placed inside or next to the area requiring treatment. The direction and shape of the radiation beam should be accurately controlled to ensure that the tumour receives the prescribed radiation dose, and the radiation from the beam should minimize damage to the surrounding healthy tissue, often called the organ(s) at risk (OARs). Treatment planning can be used to control radiation beam parameters, and a radiotherapy device effectuates a treatment by delivering a spatially varying dose distribution to the patient.

The present invention is for example used in connection with treatment planning of treatment provided by means of a radiotherapy system having a collimator body provided with several groups or sets of collimator passages, each set being designed to provide a radiation beam of a respective specified cross-section toward a fixed focus point. Suitably the inlet of each set of collimator passages has a pattern that essentially corresponds to the pattern of the sources on the source carrier arrangement. These sets of collimator passage inlets may be arranged so that it is possible to change from one set to another, thereby changing the resulting beam cross-section and the spatial dose distribution surrounding the focus point. The number of sets of collimator passages with different diameter may be more than two, such as three or four, or even more. A typical embodiment of the collimator comprises eight sectors each having four different states (beam-off, 4 mm, 8 mm, and 16 mm). The sectors can be adjusted individually, i.e. different states can be selected for each sector, to change the spatial distribution of the radiation about the focus point.

The present invention may be used in treatment planning for intensity modulated radiation therapy (IMRT) treatment.

The present invention may further be used in brachytherapy. Brachytherapy is a form of radiotherapy where a sealed radiation source is placed inside or next to the area requiring treatment. Brachytherapy involves the precise placement of short-range radiation-sources (radioisotopes, Iodine-125 for instance) directly at the site of the cancerous tumour. Brachytherapy treatment planning often involves optimization methods to calculate the dwell times and dwell positions of the radioactive source along specified applicator paths. Inverse planning methods for brachytherapy aim at obtaining adequate target coverage and maximum sparing of critical structures. In geometric optimization, the relative dwell times are determined by the geometry of the implant by assigning an individual weighting factor for the dwell time at each dwell position that is inversely proportional to the dose contribution from neighboring source locations.

Hence, the optimization problem, which in preferred embodiments is a convex optimization problem, steers the delivered radiation according to the objectives and dose profiles for specific treatment configurations including source strengths and/or dwell times are calculated using the optimization problem. Thereafter, a treatment plan, including determining the radiation dose profiles to be delivered during treatment based on the treatment configurations can be created, wherein each radiation dose profile is modelled by a spatial dose volume distribution of radiation, the shape of the spatial distribution depending on the settings and an optimal treatment plan that satisfies the criteria can be selected.

According to an aspect of the present invention, there is provided a method for dose or treatment planning for a radiotherapy system comprising a radiotherapy unit, wherein a spatial dose delivered can be changed by adjusting beam shape settings and delivered radiation is determined using an optimization problem that steers the delivered radiation according to objectives reflecting criteria for regions of interest that include at least one of: at least one target to be treated during treatment of the patient, organs at risk and/or healthy tissue. The method comprises the steps of: estimating a voxel set receiving a higher dose than a predetermined threshold dose level, which voxel set includes voxels from at least one target volume. Further, a low dose voxel set is determined and a frame description for the voxels in the low dose voxel set are provided where voxels receiving a dose exceeding a predetermined threshold value is penalized according to the frame description such that the dose delivered to the low dose voxel set is suppressed. The frame description is then used in the optimization problem that steers the delivered radiation.

The optimization problem, which in preferred embodiments is a convex optimization problem, steers the delivered radiation according to the objectives and dose profiles for specific treatment configurations including beam shape settings for the radiation dose profiles are calculated using the optimization problem. Thereafter, a treatment plan, including determining the radiation dose profiles to be delivered during treatment based on the treatment configurations can be created, wherein each radiation dose profile is modelled by a spatial dose volume distribution of radiation, the shape of the spatial distribution depending on the beam shape settings and an optimal treatment plan that satisfies the criteria can be selected. According to another aspect of the present invention, there is provided a method for treatment planning for a radiotherapy system comprising a radiotherapy unit having a fixed radiation focus point, wherein a spatial dose distribution surrounding the focus point can be changed by adjusting beam shape setting, including collimator settings. The collimator is arranged in sectors and having a plurality of collimator passage inlets directing radiation emanating from radioactive sources of a source carrier arrangement of the therapy system to the focus point. The comprises the steps of estimating a voxel set receiving a higher dose than a predetermined threshold dose level and the voxel set includes at least one target volume. Then, a low dose voxel set is determined and a frame description reflecting the criteria for the voxels in the low dose voxel set such that the dose delivered to the low dose voxel is suppressed. The frame description is then used in the optimization problem that steers the delivered radiation.

The optimization problem, which in preferred embodiments is a convex optimization problem, steers the delivered radiation according to the objectives and dose rates are calculated for specific treatment configurations including sector and collimator settings and irradiation time for isocenters using the optimization problem. Then, treatment plans can be created including determining shots to be delivered during treatment based on the treatment configurations, wherein each shot is modelled by a spatial dose volume distribution of radiation represented by a three-dimensional voxel representation, wherein the shape of the spatial distribution depending on the specific sector and collimator setting and irradiation time. Finally, an optimal treatment plan that satisfies the criteria can be selected.

According to embodiments of the present invention, a dose distribution is estimated; a first estimate of the low dose voxel set is determined; at least one optimization with either weight settings to be used in a final optimization or with standardized weight settings is performed, based on the optimized dose distribution in a preceding optimization step, the low dose voxel set defined as the volume between two dose levels is updated; the frame description is modified according to updated low dose voxel set is modified; and a final optimization using the updated low dose voxel set and modified frame description from the preceding optimization is performed.

In embodiments of the present invention, wherein the dose distribution is estimated by estimating the dose distribution outside each target independently or estimating a combined dose distribution outside the targets.

In particular, a low dose ring or volume is generated using an iterative approach. First, a dose distribution $d_i(r)$ outside target $i$ is estimated for each of the N target(s), i.e. $i=1, \ldots, N$. The estimate may be dependent on geometric factors e.g. target area A, target volume V and a vector r from a point on the target to the position in question (or derived properties such as the distance and/or direction from the target). In addition, the dose distribution estimate may be scaled with the prescription dose, $D_T$. If there is more than one target, all dose distributions outside the targets are combined by a summation that is possibly weighted using weights w. In one embodiment, the combined dose distribution is given by $$d(r) = \Sigma_{i=1}^{N} w_i \cdot D_{T_i} \cdot d_i(A_i, V_i, r),$$

Based on the combined dose distribution, a first estimate of the low dose volume is determined. In examples, the volume between two dose levels, for example these levels can be chosen as 40% and 60% of the smallest prescription dose. Then, the frame description is modified by e.g. adding a penalization term in the objective function penalizing voxels with dose exceeding a threshold dose, $D_{lr}$. E g it could be:

$$\frac{w_{lr}}{N_{lr} * D_{lr}} \sum_{i=1}^{N_{lr}} \max((\varphi x)_i - D_{lr}, 0),$$

where $w_{lr}$ is the weight, $N_{lr}$ is the number of voxels in the low dose volume. In principle the threshold dose in the low dose volume possibly can be dependent on the distance from the surface. Then, the optimization is performed with either weight settings to be used in the final optimization problem or with standardized weight settings. Thereafter, the algorithm determines whether the iterative process is finished or not, for example, after a predetermined number of iterations. If yes, a final treatment plan optimization can be performed using the low dose volume. Otherwise, based on the optimized dose distribution in the preceding optimization step, an updated low dose volume is defined as the volume between two dose levels, possibly the same as earlier and the contribution to the frame description is modified accordingly. A final treatment plan optimization is performed using the low dose volume from the iterative optimization step.

According to embodiments of the present invention, the method further includes determining a low dose voxel set by applying predetermined dose distributions.

In embodiments of the present invention, the step of determining a low dose voxel set by applying predetermined dose distributions includes calculating a first shell surface outside the voxel set based on a dose level that is higher than the threshold dose level, calculating a second shell surface outside the voxel set based on a dose level that is lower than the threshold dose level; and defining the low dose voxel set as the voxel set between the first and second shell surfaces.

According to embodiments of the present invention, the step of determining a low dose voxel set includes calculating a first shell surface outside the voxel set based on a predetermined geometry, calculating a second shell surface outside the voxel set based on a predetermined geometry and defining the low dose voxel set as the voxel set between the first and second shell surfaces.

In embodiments of the present invention, calculating the first shell surface outside the voxel set includes uniformly contracting an outer surface of the voxel set receiving a higher dose than a predetermined threshold dose level.

In embodiments of the present invention, calculating the second shell surface outside the voxel set includes uniformly expanding an outer surface of the voxel set receiving a higher dose than a predetermined threshold dose level.

In embodiments of the present invention, the method further comprises finding the isocenter locations, determining the shot collimator configurations for all isocenter locations, setting dose to be delivered to the at least one target including determining irradiation times for all shots to be delivered, and calculating a dose distribution based on the determined shot configurations and dose to be delivered.

In embodiments of the present invention, the low dose voxel set is a spherical shell having a uniform voxel thickness.

According to embodiments of the present invention, the calculating steps include applying a distance model according to:

$$\delta_r = Q V_{ad}^{1/3},$$

where Q may be a constant or include geometry factors and/or dose distribution factors, $V_{ad}$ is the volume of the voxel set receiving a higher dose than a predetermined threshold dose level, and where $\delta_r$ corresponds to the expanded or contracted distance of the outer surface of the voxel set.

In embodiments of the present invention, the calculating steps include applying a distance model according to:

$$\delta_r \sim \left(\frac{\delta D}{D_{F\,ad}}\right) V_{ad}^{1/3},$$

wherein $D_{F,ad}$ is the isodose in the voxel set receiving a higher dose than a predetermined threshold dose level, $\delta D$ is the predetermined dose distribution variation, $V_{ad}$ is voxel set receiving a higher dose than a predetermined threshold dose level.

According to embodiments of the present invention, the method further comprises calculating dose profiles for specific treatment configurations including beam shape settings for the radiation dose profiles using the optimization problem, creating treatment plans including determining the radiation dose profiles to be delivered during treatment based on the treatment configurations, wherein each radiation dose profile is modelled by a spatial dose volume distribution of radiation, the shape of the spatial distribution depending on the beam shape settings; and selecting an optimal treatment plan that satisfies the criteria.

In embodiments of the present invention, the method comprises calculating dose rates for specific treatment configurations including sector and collimator settings and irradiation time for the isocenters using the optimization problem, creating treatment plans including determining shots to be delivered during treatment based on the treatment configurations, wherein each shot is modelled by a spatial dose volume distribution of radiation, the shape of the spatial distribution depending on the specific sector and collimator setting and irradiation time, and selecting an optimal treatment plan that satisfies the criteria.

According to embodiments of the present invention, the method further comprises defining a set of beam directions, modelling radiation dose profiles to be delivered to the target as a plurality of beamlets each having a beamlet intensity, setting a number of objectives reflecting criteria for the target, providing a optimization problem that steers the delivered radiation according to the objectives so as to create fluence maps, wherein the fluence maps define the beamlet intensities for each of the beamlets, creating treatment plans based on fluence maps and criteria for the target, and selecting an optimal treatment plan that satisfies the criteria.

According to embodiments of the present invention, the method comprises positioning of radiation source(s) relative to the patient, including generating fixed isocenter positions.

In embodiments of the present invention, the radiation source positions are generated as a set of continuous points in the target volume based on basis functions, wherein the points are fixed during the treatment planning.

According to embodiments of the present invention, the objectives include delivered dose to target, delivered dose to a boundary space surrounding the target, delivered dose to regions classified as a risk organ, and/or beam-on time penalization.

An optimized dose plan determined by means of the present invention, may be transferred to a radiotherapy system for use in the treatment of the patient. The dose plan determined by the invention may also or alternatively be used as input in a treatment optimization procedure where the number of shots, position of the shots and the shot sizes defined during the volume filling according to the invention serves as basis in an optimization of the number of shots, the position and the beam-on time of the respective shots and the shots sizes.

According to still another aspect of the present invention, there is provided a treatment planning computer structure in which the method according to the present invention may be implemented.

In embodiments of the present invention, the treatment plan computer structure may utilize methods according to the present invention and may be integrated into a system for delivering intensity modulated radiation treatment (IMRT) including a radiation source that generates at least one radiation beam. A beam shaping device, e.g. a multi-leaf collimator or a conical collimator, may be disposed between the radiation source and the patient. The collimator is communicatively connected to the treatment planning computer structure and is configured to modify the plurality of beamlets to deliver according to optimal treatment plan, i.e. a fluence map based on the beam shape settings determined, to the patient.

In embodiments of the present invention, a low dose voxel set is determined based on a prediction made using a machine learning algorithm trained on a database of treatment plans. The machine learning algorithm could be, for example, a linear regression model, a logistic regression model, a support vector machine, a Gaussian process model, a random forest, a Markov random field, a conditional random field, an artificial neural network, or a deep structured learning network such as a convolutional neural network.

In further embodiments of the present invention, the treatment plan computer structure may utilize methods according to the present invention may be integrated into a radiotherapy system having a collimator body provided with several groups or sets of collimator passages, each set being designed to provide a radiation beam of a respective specified cross-section toward a fixed focus point. Suitably the inlet of each set of collimator passages has a pattern that essentially corresponds to the pattern of the sources on the source carrier arrangement. These sets of collimator passage inlets may be arranged so that it is possible to change from one set to another, thereby changing the resulting beam cross-section and the spatial dose distribution surrounding the focus. The collimator body is communicatively connected to the treatment planning computer structure to deliver according to optimal treatment plan to the patient.

As the skilled person realizes, steps of the methods according to the present invention, as well as preferred embodiments thereof, are suitable to realize as computer program or as a computer readable medium.

Further objects and advantages of the present invention will be discussed below by means of exemplifying embodiments.

DETAILED DESCRIPTION OF THE DRAWINGS

Figure 1A:
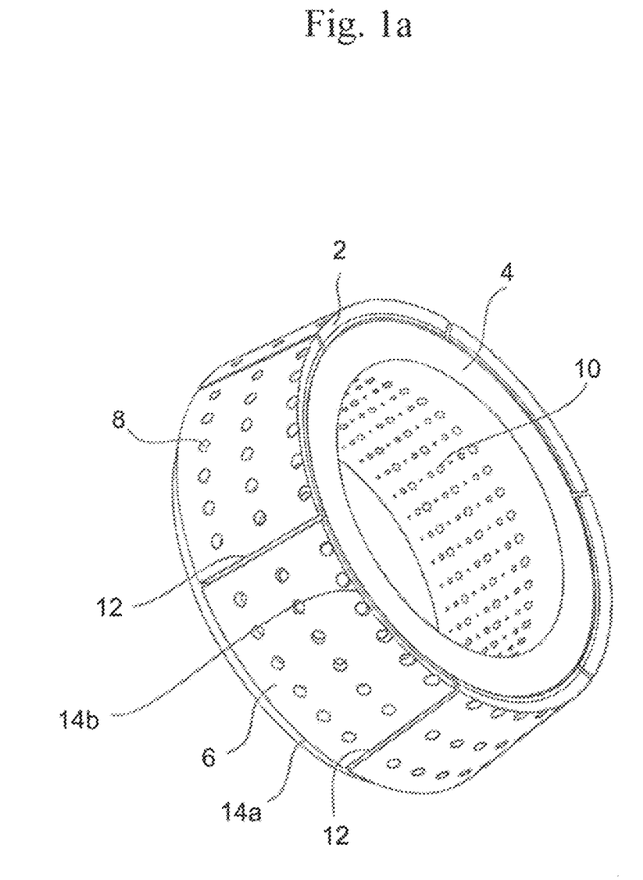
FIG. 1a is a perspective view of an assembly comprising a source carrier arrangement surrounding a collimator body in which the present invention may be used.
Figure 1B:
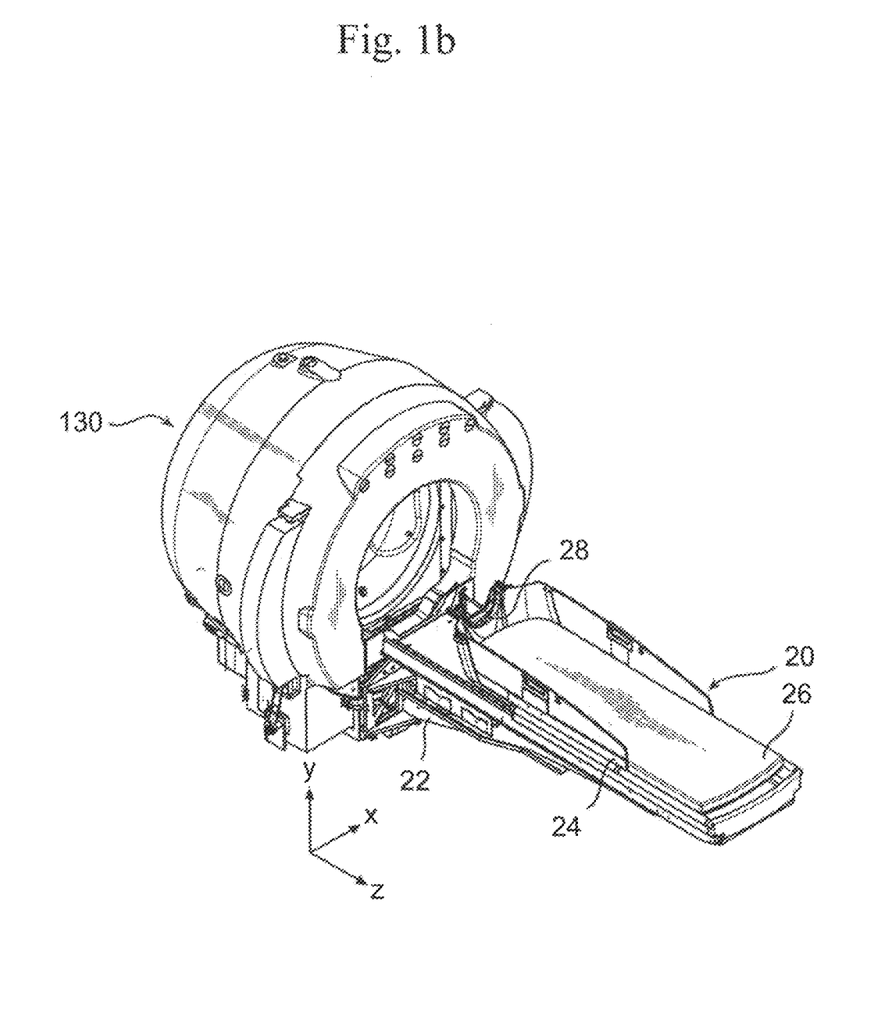
FIG. 1b shows a radiotherapy device in which the assembly of FIG. 1 may be used.

With reference first to FIGS. 1a and 1b, an exemplary radiotherapy device in which a treatment plan developed using the present invention can be used for treatment of a patient.

FIG. 1a is a perspective view of an assembly comprising a source carrier arrangement 2 surrounding a collimator body 4. The source carrier arrangement 2 and the collimator body 4 both have the shape of a frustum of a cone. The source carrier arrangement 2 comprises six segments 6 distributed along the annular circumference of the collimator body 4. Each segment 6 has a plurality of apertures 8 into which containers containing radioactive sources, such as cobalt, are placed. The collimator body 4 is provided with collimator passages or channels, internal mouths 10 of the channels are shown in the figure.

Each segment 6 has two straight sides 12 and two curved sides 14a, 14b. One of the curved sides 14a forms a longer arc of a circle, and is located near the base of the cone, while the other curved side 14b forms a shorter arc of a circle. The segments 6 are linearly displaceable, that is they are not rotated around the collimator body 4, but are instead movable back and forth along an imaginary line drawn from the center of the shorter curved side 14b to the center of the longer curved side 14a. Such a translation displacement has the effect of a transformation of coordinates in which the new axes are parallel to the old ones.

As can be seen from FIG. 1a there is a larger number of internal mouths 10 or holes of the collimator passages than the number of apertures 8 for receiving radioactive sources. In this particular case there are three times as many collimator passages as there are apertures for receiving radioactive sources, such as e.g. 180 apertures and 540 collimator passages. The reason for this is that there are three different sizes of collimator passages in the collimator body 4, or rather passages which direct radiation beams with three different diameters, toward the focus point. The diameters may e.g. be 4, 8 and 16 mm. The three different types of collimator passages are each arranged in a pattern which corresponds to the pattern of the apertures in the source carrier arrangement. The desired size or type of collimator passage is selected by displacing the segments 6 of the source carrier arrangement linearly along the collimator body so as to be in register with the desired collimator passages.

In FIG. 1b, a radiotherapy system including a radiotherapy device 130 having a source carrier arrangement as shown in FIG. 1b, and a patient positioning unit 20 is shown. In the radiotherapy unit 130, there are thus provided radioactive sources, radioactive source holders, a collimator body, and external shielding elements. The collimator body comprises a large number of collimator channels directed towards a common focus point, as shown in FIG. 1b.

The patient positioning unit 20 comprises a rigid framework 22, a slidable or movable carriage 24, and motors (not shown) for moving the carriage 24 in relation to the framework 22. The carriage 24 is further provided with a patient bed 26 for carrying and moving the entire patient. At one end of the carriage 24, there is provided a fixation arrangement 28 for receiving and fixing a patient fixation unit or interface unit. The coordinates of the fixation unit are defined by a fixation unit coordinate system, which through the fixed relationship with the treatment volume also is used for defining the outlines of the treatment volume. In operation, the fixation unit, and hence the fixation unit coordinate system, is moved in relation to the fixed radiation focus point such that the focus point is accurately positioned in the intended coordinate of the fixation unit coordinate system.

Figure 2A:
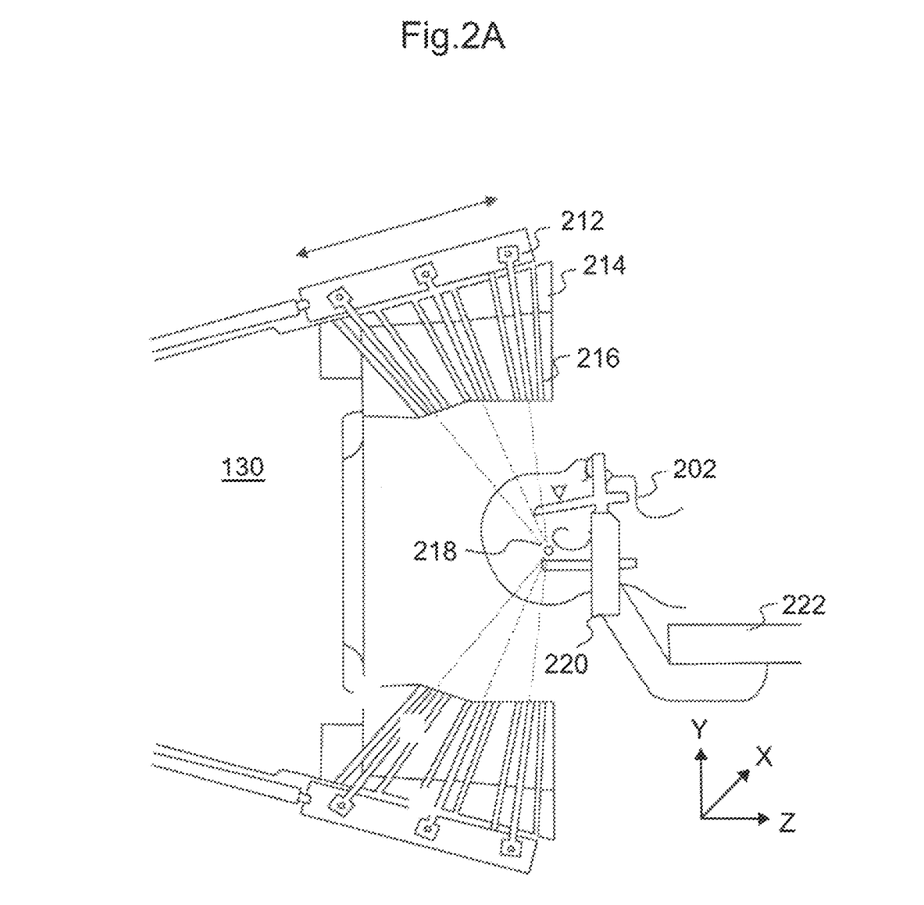
FIG. 2a shows a radiotherapy device, a Gamma Knife, in which the present invention may be used.

FIG. 2a illustrates a radiotherapy device 130, a Gamma Knife in which the present invention can be used. A patient 202 may wear a coordinate frame 220 to keep stable the patient's body part (e.g. the head) undergoing surgery or radiotherapy. Coordinate frame 220 and a patient positioning system 222 may establish a spatial coordinate system, which may be used while imaging a patient or during radiation surgery. Radiotherapy device 130 may include a protective housing 214 to enclose a plurality of radiation sources 212 for generation of radiation beams (e.g. beamlets) through beam channels 216. The plurality of beams may be configured to focus on an isocenter 218 from different locations. While each individual radiation beam may have relatively low intensity, isocenter 218 may receive a relatively high level of radiation when multiple doses from different radiation beams accumulate at isocenter 218. In certain embodiments, isocenter 218 may correspond to a target under surgery or treatment, such as a tumour.

Figure 2B:
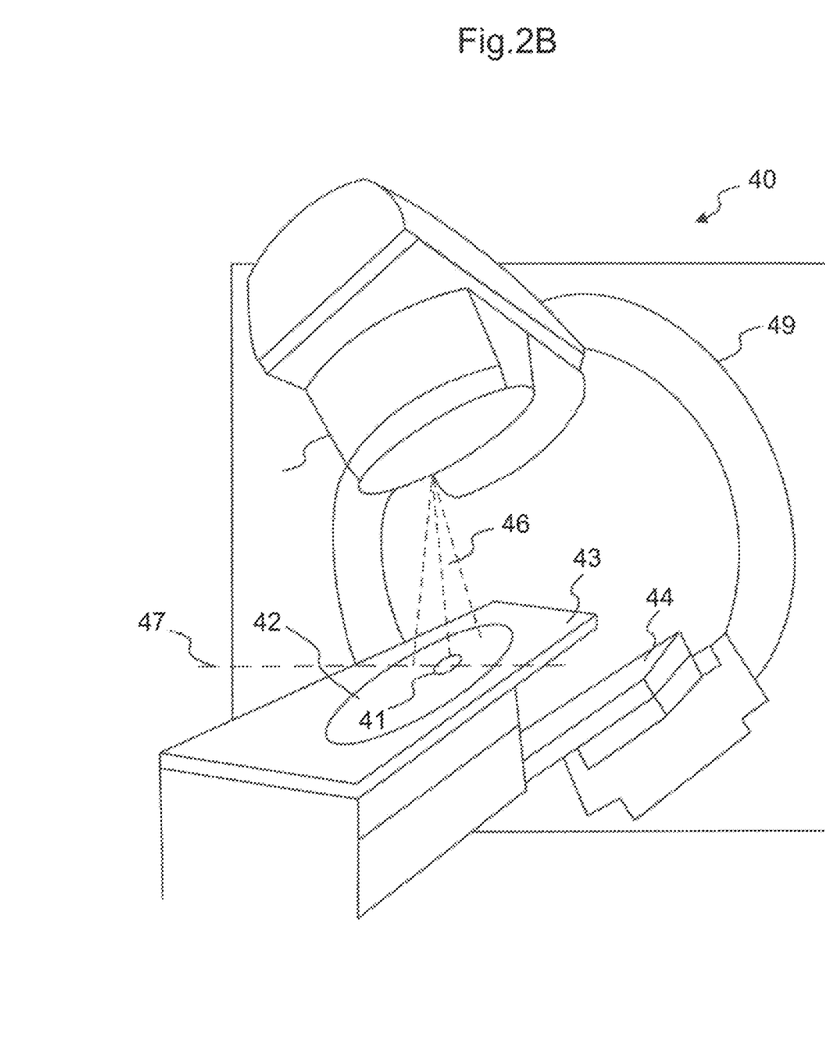
FIG. 2b shows another radiotherapy device, a linear accelerator, in which the present invention can be used.

FIG. 2b illustrates another radiotherapy device 40, a linear accelerator 10 in which the present invention can be used. Using a linear accelerator 40, a patient 42 may be positioned on a patient table 43 to receive the radiation dose determined by the treatment plan. Linear accelerator 40 may include a radiation head 45 that generates a radiation beam 46. The entire radiation head 45 may be rotatable around a horizontal axis 47. In addition, below the patient table 43 there may be provided a flat panel scintillator detector 44, which may rotate synchronously with radiation head 45 around an isocenter 41. The intersection of the axis 47 with the center of the beam 46, produced by the radiation head 45 is usually referred to as the "isocenter". The patient table 43 may be motorized so that the patient 42 can be positioned with the tumour site at or close to the isocenter 41. The radiation head 45 may rotate about a gantry 47, to provide patient 42 with a plurality of varying dosages of radiation according to the treatment plan.

Figure 3:
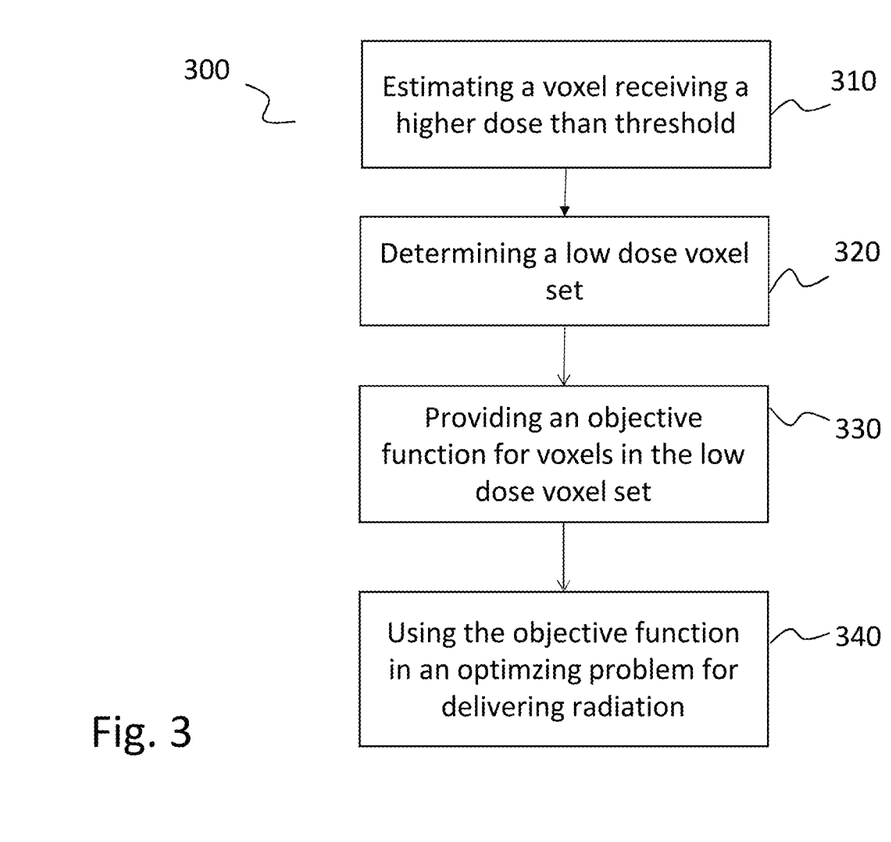
FIG. 3 is a flow diagram illustrating an embodiment of the present invention.

With reference now to FIG. 3, a general method 300 according to the present invention will be described. The method may be used for treatment planning, for example, in brachytherapy, radiosurgery, and intensity modulated radiotherapy as well as in Volumetric Modulated Arc Therapy. In a linear accelerator, electron beams are generated by an electron accelerator including an electron gun, a wave guide and a guide magnet. The electron beam impinges on a target made of high atomic number materials thereby creating ionizing radiation. Ionizing radiation can be modeled as a plurality of beamlets each having a beamlet intensity that can be modelled according to a fluence map. The fluence map is determined in the optimization. Moreover, the method may also be used in treatment planning for radiotherapy system having a collimator body provided with several groups or sets of collimator passages, each set being designed to provide a radiation beam of a respective specified cross-section toward a fixed focus point. Suitably the inlet of each set of collimator passages has a pattern that essentially corresponds to the pattern of the sources on the source carrier arrangement. These sets of collimator passage inlets may be arranged so that it is possible to change from one set to another, thereby changing the resulting beam cross-section and the spatial dose distribution surrounding the focus point. The number of sets of collimator passages with different diameter may be more than two, such as three or four, or even more. A typical embodiment of the collimator comprises eight sectors each having four different states (beam-off, 4 mm, 8 mm, and 16 mm). The sectors can be adjusted individually, i.e. different states can be selected for each sector, to change the spatial distribution of the radiation about the focus point.

First in the method 300, in step 310, a voxel set receiving a higher dose than a predetermined threshold dose level is identified, wherein the voxel set includes voxels from at least one target volume.

Then, at step 320, a low dose voxel set is determined. This can be done by applying predetermined dose distributions. In one embodiment of the present invention, this may include calculating a first shell surface outside the voxel set based on a dose level that is higher than the threshold dose level and calculating a second shell surface outside the voxel set based on a dose level that is lower than the threshold dose level. Then, the low dose voxel set is defined as the voxel set between the first and second shell surfaces, respectively.

In another embodiment of the present invention, this may include calculating a first shell surface outside the voxel set based on a predetermined geometry and calculating a second shell surface outside the voxel set based on a predetermined geometry and defining the low dose voxel set as the voxel set between the first and second shell surfaces, preferably.

At step 330, an objective function for the voxels in the low dose voxel set is provided where voxels receiving a dose exceeding a predetermined threshold value is penalized such that the dose delivered to the low dose voxel set is suppressed.

Thereafter, at step 340, the objective function is used in the optimization problem that steers the delivered radiation. Hence, the optimization problem, which in preferred embodiments is a convex optimization problem, steers the delivered radiation according to the objectives and dose profiles for specific treatment configurations including beam shape settings for the radiation dose profiles are calculated using the optimization problem. Thereafter, a treatment plan, including determining the radiation dose profiles to be delivered during treatment based on the treatment configurations can be created, wherein each radiation dose profile is modelled by a spatial dose volume distribution of radiation, the shape of the spatial distribution depending on the beam shape settings and an optimal treatment plan that satisfies the criteria can be selected.

Figure 4:
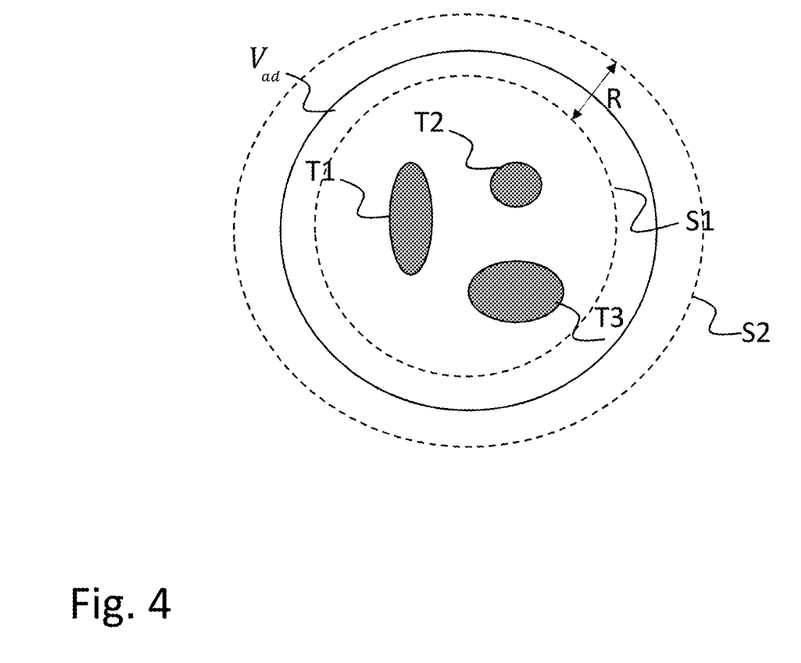
FIG. 4 shows the geometry of an inverse planning problem in a simplified two-dimensional illustration according to another embodiment of the present invention.

Now, the method according to the present invention will be described in more detail with reference, in particular, to FIG. 4. However, it should be noted that FIG. 4 shows the geometry of in a simplified two-dimensional illustration. The structures are shown as rings but since the target volumes is three-dimensional, the rings are consequently shells or sphere layers shapes and encompasses the target volume (or tumour value).

There is an abundance of clinical data showing that adverse cognitive effects may occur if large volumes, $V_{ad}$, of normal tissue is irradiated by relatively low dose. In particular, this is the case when multiple targets are close to each other. The main problem is that the set of voxels, with volume equal to $V_{ad}$, depends on the dose distribution and will change during the optimization, leading to a non-convex optimization problem which is in general difficult to solve. To achieve a convex formulation it is therefore necessary to have a fixed geometry in which dose is penalized.

According to the present invention, a volume filling procedure or fill algorithm is applied, for example, a fill algorithm used in the Leksell GammaPlan. One example of a suitable fill algorithm is described in a co-pending, not yet published, patent application by the same applicant.

Based on the use of the fill algorithm, a fixed low dose ring, R as shown in FIG. 4, of voxels can be created in the volume surrounding at least one target (T1, T2, T3). The voxels of this fixed volume can then be penalized giving an efficient low dose penalization. If there is assumed that there is a pair ($V_{ad}$, $D_{ad}$) where $D_{ad}$ is the dose at which adverse effects are significant if the volume is at least $V_{ad}$, see FIG. 4. For instance, there is clinical evidence suggesting an increased risk of radionecrosis if the volume receiving more than 10 Gy exceeds 13 cc, but the user could specify other values. According to the present invention, such adverse effects can be significantly reduced or eliminated by introducing a penalty term in the optimization problem. As mentioned above, a fill algorithm is used first, which is a pre-step to the optimization. In addition to providing the isocenter locations, the fill algorithm also gives the shot collimator configuration for each isocenter. By setting the prescription dose forcing the weights to be 1 for all shots, a realistic dose distribution can be calculated. To suppress doses to large volume a low dose ring is created and the algorithm for creating the low dose ring consists of the following steps. A fill algorithm is thus used to find isocenter locations and to determine shot collimator configurations for all isocenter locations. Prescription doses for the target(s), T1, T2, T3, are set. This gives irradiation times for all shots. Then, the dose distribution is calculated from the above configuration.

Thereafter, the voxels, $SV_{ad}$, in the the 3D isodose volume of the dose distribution having a volume equal to $V_{ad}$ (after having added the target volumes) are identified. Then, a ring of voxels, R ($R=2\delta_r$) is defined as the set difference between a contraction and an expansion of $SV_{ad}$, see FIG. 4, using, for example, a distance model:

$$\delta_r = \frac{1}{3\alpha}\left(\frac{\delta D}{D_{F\,ad}}\right)V_{ad}^{\frac{1}{3}},$$

$$\alpha \approx 0.65$$

$$\delta D_{contract} = 1\ Gy$$

$$\delta D_{expand} = 1\ Gy$$

Here $D_{F,ad}$ is the isodose in Gy corresponding to $V_{ad}$. A "ring size" corresponding to 1 Gy is a reasonable choice to include various dose distributions without introducing too many voxels in the optimization. However, it should be noted that the distance model shown above is one specific example, and according to other embodiments of the present invention, the calculating steps may include applying a more general distance model according to:

$$\delta_r = QV_{ad}^{1/3},$$

where Q may be a constant or include geometry factors and/or dose distribution factors, $V_{ad}$ is the volume of the voxel set receiving a higher dose than a predetermined threshold dose level, and where $\delta_r$ corresponds to the expanded or contracted distance of the outer surface of the voxel set. In embodiments of the present invention, the calculating steps include applying a distance model according to:

$$\delta_r \propto \left(\frac{\delta D}{D_{Fad}}\right) V_{ad}^{1/3},$$

wherein $D_{F,ad}$ is the isodose in the voxel set receiving a higher dose than a predetermined threshold dose level, $\delta D$ is the predetermined dose distribution variation, $V_{ad}$ is voxel set receiving a higher dose than a predetermined threshold dose level.

Then, a penalization term is added in the objective function penalizing voxels with dose exceeding a threshold dose. In embodiments of the present invention, it may be in the following form:

$$\frac{w_{lr}}{N_r * D_{ad}} \sum_{i=l}^{N_{lr}} \max((D)_i - D_{ad}, 0)$$

where the sum runs over voxels in the low dose ring and $w_{lr}$ is the optimization weight. This ring is treated in the same way as the outer ring(s) in the optimization.

Figure 5:
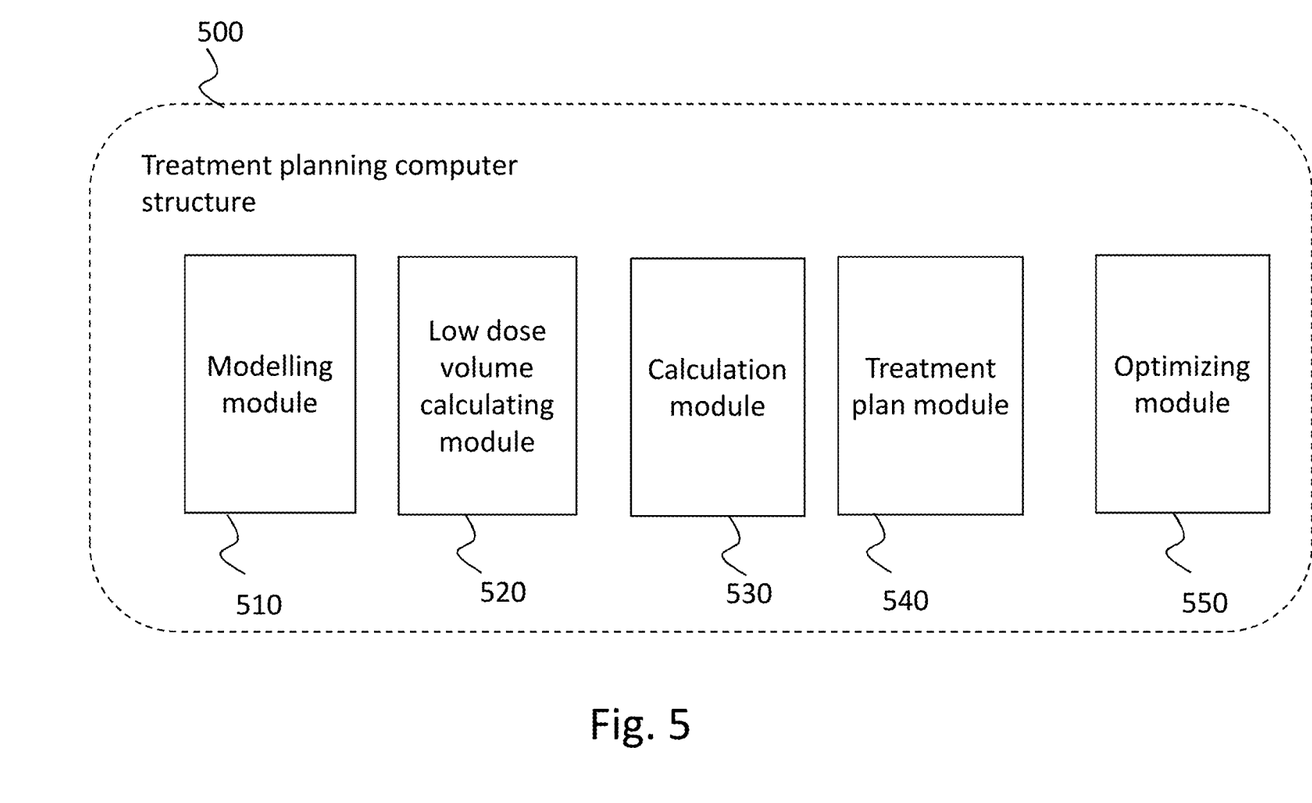
FIG. 5 shows an embodiment of a treatment planning computer structure according to the present invention.

Turning now to FIG. 5, a treatment planning computer structure in which the method according to the present invention may be implemented will be described. The treatment planning computer structure 500 may include a modelling module 510 configured for modelling a volume of a patient as a three-dimensional voxel representation or for obtaining such a three-dimensional voxel representation, wherein the volume includes a target volume to be treated during a treatment of the patient in a radiotherapy unit.

A low dose volume calculating module 520 calculates or determines a low dose volume by estimating a voxel volume set receiving a higher dose than a predetermined boundary dose level, the voxel volume set including at least one target volume, determining a low dose voxel volume set by applying predetermined varied dose distributions and applying an objective function for the voxels in the low dose voxel volume set where voxels receiving a dose exceeding a predetermined threshold value is penalized such that the dose delivered to the low dose voxel volume is suppressed. In more detail, the low dose volume calculating module applies the method or procedure described above with reference to FIG. 4.

Further, a calculation module 530 configured for generating radiation dose profiles to be delivered to the target, for providing a convex optimization problem including the objective function for the low dose volume that steers the delivered radiation according to the objectives, and for calculating dose profiles for specific treatment configurations including beam shape settings for the radiation dose profiles are calculated using the convex optimization problem. A treatment plan module 540 is configured for creating treatment plans including determining the radiation dose profiles to be delivered during treatment based on the treatment configurations, wherein each radiation dose profile is modelled by a spatial dose volume distribution of radiation represented by a three-dimensional voxel representation, the shape of the spatial distribution depending on the beam shape settings. An optimizing module 550 is configured for selecting an optimal treatment plan that satisfies the clinical criteria. In embodiments of the present invention, the optimization, i.e. selecting an optimal treatment plan that satisfies the clinical criteria, is performed and then the treatment plan including determining the radiation dose profiles to be delivered during treatment based on the treatment configurations is created.

In embodiments of the present invention, the treatment plan computer structure 500 may utilize a method as described in FIG. 3 or 5 and may be integrated into a system for delivering intensity modulated radiation treatment (IMRT) including a radiation source that generates at least one radiation beam and a structure for generating a plurality of beamlets. A beam shaping device, e.g. a multi-leaf collimator or a conical collimator, may be disposed between the radiation source and the patient. The collimator is communicatively connected to the treatment planning computer structure and has a plurality of leaves for modifying the plurality of beamlets to deliver according to optimal treatment plan, i.e. a fluence map based on the beam shape settings determined, to the patient.

The methods described herein according to the present invention may furthermore be used in combination with inner and outer shells that encompasses the target and are associated with each target where an inner shell promotes selectivity and tan outer shell promotes gradient index, respectively. The frame description for each shell is formulated so that each voxel can be individually considered. According to an embodiment, the terms of the frame description is an approximation of an integral, namely a sum where the terms correspond to the voxels at distances r from the outer surface(s) of the target(s) volume and may be given by:

$$\frac{1}{M}\sum_{j=1}^{M} \frac{1}{D(r)N_j} \sum_{i=1}^{N_j} w_{ij} \max((\varphi_j x)_i - D(r), 0),$$

where x is the irradiation times for each isocenter, sector, and collimator setting, D(r) is a function describing the desired dose as a function of the distances from the target surfaces, r is the vector of distances from the target surface (s), $N_j$ is the number of voxels at distance $r_j$ and $w_{ij}$ is a scalar weight, which in embodiments can be varied voxel-by-voxel. In embodiments of the present invention, the term D(r) is used, describing that the desired dose varies in different directions. Two shells are applied having a size or volume that depend on the volume of the target. Penalizing dose in these two shells will correspond to promoting the two non-convex quantities selectivity and gradient index, respectively. The size or volume of the outer shell is preferably chosen so that a desired gradient index can be achieved.

The objective function may be formulated voxel-by-voxel for the target and the two encompassing shells. According to embodiments of the present invention, a minimal objective function for one target and thus two shells, which easily can be generalized to more than one target, with neither OAR nor beam-on time penalization, can be formulated as follows:

$$\arg \min_x f =$$

$$\frac{w_1}{D_T N_T} \sum_{i=1}^{N_T} \max(D_T - (\varphi_T x)_i, 0) + \frac{w_2}{D_T N_{IR}} \sum_{i=1}^{N_{IR}} \max((\varphi_{IR} x)_i - D_T, 0) + +$$

$$\frac{w_3}{(D_T/2)N_R} \sum_{i=1}^{N_R} \max\left((\varphi_R x)_i - \frac{D_T}{2}, 0\right) x \geq 0,$$

where x is the irradiation times for each isocenter, sector and collimator setting, $w_1$, $w_2$, $w_3$ are the weights for the target, inner and outer ring respectively. $D_T$ is the prescription dose, $N_i$ is the number of target voxels in the structure i∈{T, IR, OR} and $\varphi_i$ is the dose rate in the respective structure. The first term penalizes underdosing of the target, the second term penalizes overdosing of the inner shell and the third term penalizes dose in the outer shell that exceeds $D_T/2$, where the gradient index is defined as the volume with dose exceeding $D_T/2$ over volume of the dose exceeding $D_T$. The three terms are good convex surrogates for coverage, selectivity and gradient index, respectively. The objective function is a weighted sum where the three weights $w_1$, $w_2$, $w_3$ governs the relative importance of the different objectives, and thus, the importance of coverage, selectivity and gradient index respectively. With one weight, or at least one weight, corresponding to each clinical metric, the translation of the clinical objectives to the desired plan qualities can be obtained by adjusting weights of the objective function before the optimization is performed.

Figure 6:
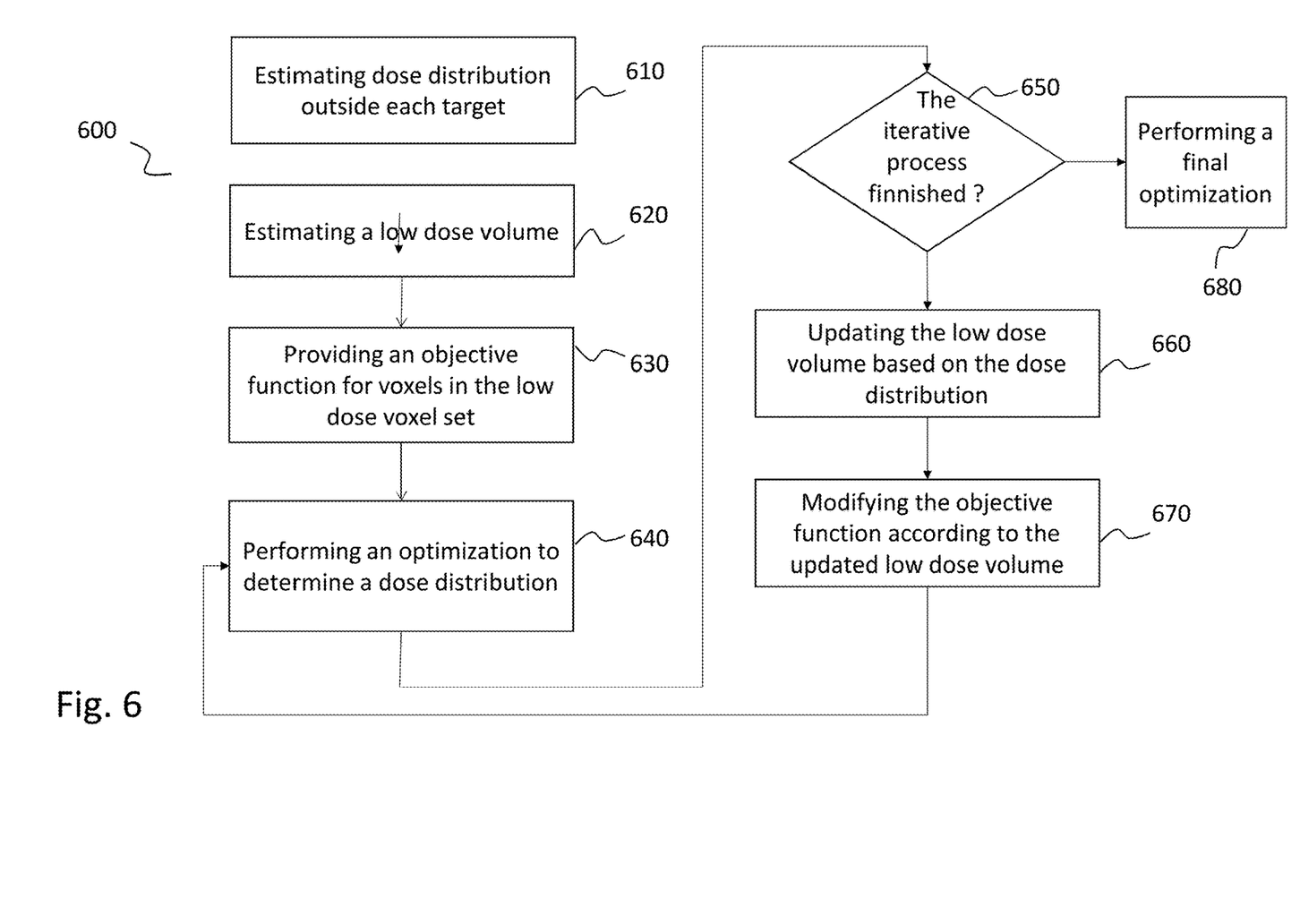
FIG. 6 is a flow diagram illustrating a further embodiment of the present invention.

According to embodiments of the present invention, a low dose ring or volume is generated using an iterative approach. This approach 600 will now be described with reference to FIG. 6. First, at step 610, a dose distribution outside each of the target(s) is estimated according to:

$$D_T * d_i(A, V, r),$$

which may be dependent on the geometric factors, the distance from the target and possibly the direction from the target. In addition, the dose distribution estimate is scaled with the prescription dose, $D_T$. It is assumed that the dose on the target surface is $D_T$. If there is more than one target, all dose distributions outside the targets are added together. The addition could possibly be weighted.

Based on the combined dose distribution, a first estimate of the low dose volume is determined in step 620. In examples, the volume between two dose levels, for example these levels can be chosen as 40% and 60% relative to the lowest of the prescription doses.

Then, at step 630, a penalization term is added to the frame description penalizing voxels with dose exceeding a threshold dose, $D_{lr}$. E g it could be:

$$\frac{w_{lr}}{N_{lr} * D_{lr}} \sum_{i=1}^{N_{lr}} \max((\varphi x)_i - D_{lr}, 0),$$

where $w_{lr}$ is the weight, $N_{lr}$ is the number of voxels in the low dose volume. In principle the threshold dose in the low dose volume possibly can be dependent on the distance from the surface.

Then, at step 640, the optimization is performed with either weight settings to be used in the final optimization problem or with standardized weight settings.

Thereafter, in step 650, it determined whether the iterative process is finished or not. For example, after a predetermined number of iterations. If yes, a final treatment plan optimization can be performed using the low dose volume in step 680. If no, the procedure 600 proceeds to step 660, where, based on the optimized dose distribution in the preceding optimization step, an updated low dose volume is defined as the volume between two dose levels, possibly the same as in step 620. The term in the objective function is modified accordingly in step 670.

Although an exemplary embodiment of the present invention has been shown and described, it will be apparent to those having ordinary skill in the art that a number of changes, modifications, or alterations to the inventions as described herein may be made. Thus, it is to be understood that the above description of the invention and the accompanying drawings is to be regarded as a non-limiting.

The invention claimed is:

1. A method for treatment planning in radiotherapy, wherein delivered radiation is determined using an optimization problem that steers the delivered radiation according to objectives reflecting criteria for regions of interest, that include at least one of: at least one target to be treated during treatment of the patient, organs at risk and/or healthy tissue, said method comprising the steps of:
estimating a voxel set receiving a higher dose than a predetermined threshold dose level, said voxel set including voxels from at least one target volume;
determining a low dose voxel set;
providing a frame description for the voxels in the low dose voxel set, wherein according to the frame description, the dose delivered to the low dose voxel set is suppressed; and
using said frame description in the optimization problem that steers the delivered radiation.

2. A method for treatment planning for a radiotherapy system, the radiotherapy system comprising a radiotherapy unit, wherein a spatial dose delivered can be changed by adjusting beam shape settings, wherein delivered radiation is determined using an optimization problem that steers the delivered radiation according to objectives reflecting criteria for regions of interest, that include at least one of: at least one target to be treated during treatment of the patient, organs at risk and/or healthy tissue, said method comprising the steps of:
estimating a voxel set receiving a higher dose than a predetermined threshold dose level, said voxel set including voxels from at least one target volume;
determining a low dose voxel set;
providing a frame description for the voxels in the low dose voxel set, wherein according to the frame description voxels receiving a dose exceeding a predetermined threshold value is penalized such that the dose delivered to the low dose voxel set is suppressed; and
using said frame description in the optimization problem that steers the delivered radiation.

3. The method according to claim 1, wherein the method is for treatment planning for a radiotherapy system, the radiotherapy system comprising a radiotherapy unit having a fixed radiation focus point, said method further comprising the steps of:

estimating a voxel set receiving a higher dose than a predetermined threshold dose level, said voxel set including at least one target volume;

determining a low dose voxel set;

providing a frame description for the voxels in the low dose voxel set, wherein according to the frame description voxels receiving a dose exceeding a predetermined threshold value is penalized such that the dose delivered to the low dose voxel is suppressed; and using said frame description in the optimization problem that steers the delivered radiation.

4. The method according to claim 1, further comprising:
determining a first estimate of the low dose voxel set;
performing at least one optimization with either weight settings to be used in a final optimization or with standardized weight settings;
based on the optimized dose distribution in a preceding optimization step, updating the low dose voxel set defined as the volume between two dose levels;
modifying the objective function according to updated low dose voxel set; and
performing a final optimization using the updated low dose voxel set and modified objective function from the preceding optimization.

5. The method according to claim 2, further comprising:
determining a first estimate of the low dose voxel set;
performing at least one optimization with either weight settings to be used in a final optimization or with standardized weight settings;
based on the optimized dose distribution in a preceding optimization step, updating the low dose voxel set defined as the volume between two dose levels;
modifying the objective function according to updated low dose voxel set; and
performing a final optimization using the updated low dose voxel set and modfied objective function from the preceding optimization.

6. The method according to claim 1, further comprising the step of estimating a dose distribution.

7. The method according to claim 6, wherein the dose distribution is estimated by estimating the dose distribution outside each target independently or estimating a combined dose distribution outside the targets.

8. The method according to claim 1, further including determining a low dose voxel set by applying predetermined dose distributions.

9. The method according to claim 8, wherein the step of determining a low dose voxel set by applying predetermined dose distributions includes:
calculating a first shell surface outside said voxel set based on a dose level that is higher than said threshold dose level;
calculating a second shell surface outside said voxel set based on a dose level that is lower than said threshold dose level; and
defining the low dose voxel set as the voxel set between said first and second shell surfaces.

10. The method according to claim 9, wherein calculating the first shell surface outside said voxel set includes uniformly contracting an outer surface of the voxel set receiving a higher dose than a predetermined threshold dose level.

11. The method according to claim 9, wherein calculating the second shell surface outside said voxel set includes uniformly expanding an outer surface of the voxel set receiving a higher dose than a predetermined threshold dose level.

12. The method according to claim 1, further comprising:
finding the isocenter locations;
determining the shot collimator configurations for all isocenter locations;
setting dose to be delivered to the at least one target including determining irradiation times for all shots to be delivered; and
calculating a dose distribution based on the determined shot configurations and dose to be delivered.

13. The method according to claim 1, wherein the calculating steps include applying a distance model according to:

$$\delta_r = QV_{ad}^{\frac{1}{3}},$$

where Q may be a constant or include geometry factors and/or dose distribution factors, $V_{ad}$ is the volume of the voxel set receiving a higher dose than a predetermined threshold dose level, and where $\delta_r$ corresponds to the expanded or contracted distance of the outer surface of the voxel set.

14. The method according to claim 13, wherein the calculating steps include applying a distance model according to:

$$\delta_r \propto \left(\frac{\delta D}{D_{F,ad}}\right) V_{ad}^{1/3},$$

wherein $D_{F,ad}$ is the isodose in the voxel set receiving a higher dose than a predetermined threshold dose level, $\delta D$ is the predetermined dose distribution variation, $V_{ad}$ is voxel set receiving a higher dose than a predetermined threshold dose level.

15. The method according to claim 1, further comprising:
calculating dose profiles for specific treatment configurations including beam shape settings for the radiation dose profiles using said optimization problem;
creating treatment plans including determining the radiation dose profiles to be delivered during treatment based on the treatment configurations, wherein each radiation dose profile is modelled by a spatial dose volume distribution of radiation, the shape of said spatial distribution depending on the beam shape settings; and
selecting an optimal treatment plan that satisfies the criteria.

16. The method according to claim 1, further comprising:
calculating dose rates for specific treatment configurations including sector and collimator settings and irradiation time for the isocenters using said optimization problem;
creating treatment plans including determining shots to be delivered during treatment based on the treatment configurations, wherein each shot is modelled by a spatial dose volume distribution of radiation, the shape of said spatial distribution depending on the specific sector and collimator setting and irradiation time; and
selecting an optimal treatment plan that satisfies the criteria.

17. The method according to claim 16, further comprising:

defining a set of beam directions;

modelling radiation dose profiles to be delivered to said target as a plurality of beamlets each having a beamlet intensity;

setting a number of objectives reflecting criteria for the target;

providing an optimization problem that steers the delivered radiation according to the objectives so as to create fluence maps, wherein the fluence maps define the beamlet intensities for each of said beamlets;

creating treatment plans based on fluence maps and criteria for the target; and selecting an optimal treatment plan that satisfies the criteria.

18. The method according to claim 1, further comprising positioning of radiation source(s) relative to said patient.

19. The method according to claim 18, wherein the step of positioning radiation source(s) includes generating fixed isocenter positions.

20. The method according to claim 18, wherein the radiation source positions are generated as a set of continuous points in said target volume based on basis functions, wherein the points are fixed during the treatment planning.

21. The method according to claim 1, wherein said objectives include delivered dose to target, delivered dose to a boundary space surrounding said target, delivered dose to regions classified as a risk organ, and/or beam-on time penalization.

22. The method according to claim 1, wherein determining a low dose voxel set includes determining the low dose voxel set using a trained machine learning model.

23. A treatment planning computer structure for treatment planning for radiotherapy, wherein delivered radiation is determined using an optimization problem that steers the delivered radiation according to a frame description reflecting criteria for regions of interest, that include at least one of: at least one target to be treated during treatment of the patient, organs at risk and/or healthy tissue, comprising:

a low dose volume calculating module for calculating a low dose volume by estimating a voxel volume set receiving a higher dose than a predetermined boundary dose level, the voxel volume set including at least one target volume, determining a low dose voxel volume set by applying predetermined varied dose distributions and applying a frame description for the voxels in the low dose voxel volume set where voxels receiving a dose exceeding a predetermined threshold value is penalized such that the dose delivered to the low dose voxel volume is suppressed; and a calculation module configured for generating radiation dose profiles to be delivered to the target, for providing a convex optimization problem including the frame description for the low dose volume that steers the delivered radiation according to the objectives, and for calculating dose profiles for specific treatment configurations using the convex optimization problem.

24. The treatment planning computer structure according to claim 23, further comprising:

a treatment plan module is configured for creating treatment plans including determining the radiation dose profiles to be delivered during treatment based on the treatment configurations, wherein each radiation dose profile is modelled by a spatial dose volume distribution of radiation, the shape of the spatial distribution depending on the beam shape settings; and an optimizing module is configured for selecting an optimal treatment plan that satisfies the criteria.

25. The treatment planning computer structure according to claim 23, wherein the low dose volume calculating module is configured to execute the steps of:

estimating a voxel set receiving a higher dose than a predetermined threshold dose level, said voxel set including voxels from at least one target volume;

determining a low dose voxel set;

providing a frame description for the voxels in the low dose voxel set, wherein according to the frame description, the dose delivered to the low dose voxel set is suppressed; and using said frame description in the optimization problem that steers the delivered radiation.

* * * * *

UNITED STATES PATENT AND TRADEMARK OFFICE
CERTIFICATE OF CORRECTION

PATENT NO. : 10,888,711 B2
APPLICATION NO. : 16/282169
DATED : January 12, 2021
INVENTOR(S) : Håkan Nordström et al.

Page 1 of 1

It is certified that error appears in the above-identified patent and that said Letters Patent is hereby corrected as shown below:

On the Title Page

Change:
"(73) Assignee: ELEKTA INSTRUMENTS AB, Stockholm (SE)"
To:
--(73) Assignee: ELEKTA INSTRUMENT AB, Stockholm (SE)--

Signed and Sealed this
Thirtieth Day of March, 2021

Drew Hirshfeld
*Performing the Functions and Duties of the*
*Under Secretary of Commerce for Intellectual Property and*
*Director of the United States Patent and Trademark Office*